United States Patent
Plebuch et al.

(10) Patent No.: US 8,313,753 B2
(45) Date of Patent: Nov. 20, 2012

(54) USE OF A MIXTURE OF CRYSTALS FOR STIMULATION OF THE THYMUS GLAND

(76) Inventors: Harald Plebuch, Dortmund (DE); Erika Funk, Dortmund (DE)

( * ) Notice: Subject to any disclaimer, the term of this patent is extended or adjusted under 35 U.S.C. 154(b) by 1707 days.

(21) Appl. No.: 10/486,197

(22) PCT Filed: Aug. 19, 2002

(86) PCT No.: PCT/EP02/09234
§ 371 (c)(1),
(2), (4) Date: Feb. 13, 2004

(87) PCT Pub. No.: WO03/018115
PCT Pub. Date: Mar. 6, 2003

(65) Prior Publication Data
US 2004/0237586 A1 Dec. 2, 2004

(30) Foreign Application Priority Data

Aug. 21, 2001 (DE) .............................. 201 13 519 U
Nov. 22, 2001 (DE) .............................. 201 19 039 U
Feb. 26, 2002 (DE) ................................. 102 08 018

(51) Int. Cl.
*A61K 9/00* (2006.01)

(52) U.S. Cl. ..................................................... 424/400
(58) Field of Classification Search ........................ None
See application file for complete search history.

(56) References Cited

U.S. PATENT DOCUMENTS

| | | | | |
|---|---|---|---|---|
| 3,748,712 A | * | 7/1973 | Karawin | 428/672 |
| 4,184,344 A | * | 1/1980 | Pepin | 63/31 |
| 4,809,417 A | * | 3/1989 | Normann, Jr. | 29/896.41 |
| 7,055,342 B2 | * | 6/2006 | Minassian | 63/3 |
| 2004/0197419 A1 | * | 10/2004 | Cole et al. | 424/617 |

FOREIGN PATENT DOCUMENTS

| | | |
|---|---|---|
| CH | 687438 | 12/1996 |
| DE | 3 325507 | 1/1985 |
| DE | 4 317884 | 2/1994 |
| DE | 20 103737 | 6/2001 |

OTHER PUBLICATIONS

Crystals and Gemstones, Facts about crystals and gemstones, available online Feb. 8, 1999.*

* cited by examiner

*Primary Examiner* — Anand Desai
*Assistant Examiner* — Melissa Mercier
(74) *Attorney, Agent, or Firm* — Dennison, Schultz & MacDonald

(57) ABSTRACT

A mixture of crystals comprising natural ring silicates and natural silica for stimulation of the thymus gland.

11 Claims, 3 Drawing Sheets

USE OF A MIXTURE OF CRYSTALS FOR STIMULATION OF THE THYMUS GLAND

This application is a filing under 35 USC 371 of PCT/EP02/09234 filed Aug. 19, 2002.

BACKGROUND OF THE INVENTION

The invention relates to the use of a mixture of crystals for the stimulation of the thymus gland.

It is known that, for example, yellow jasper, emerald or serpentine activates and stimulates the thymus gland (Das Große Lexikon der Heilsteine, Düfte und Kräuter (The Great Lexicon of Healing Stones, Scents and Herbs), Methusalem Verlagsgesellschaft mbH, Neu-Ulm, 1997 page 319). Aquamarine, blue tourmaline, diamonds, green tourmaline, lapis lazuli, jade or peridot also have an effect on the thymus gland. Measurements, however, showed that they only have a limited effect.

The German Utility Patent 201 03 737 refers to an arrangement for lowering the influence of devices generating electromagnetic fields on humans. It is hereby suggested to use a mixture of semiprecious stones and precious stones or crystalline minerals, whereby hematite is suggested as one of the materials and rock crystal is suggested as another one.

DE 43 17 884 A1 refers to a device for neutralizing or shielding the human body from harmful environmental influences. Here a mineral such as crystal quartz in a non-metallic body is used. DE 33 25 507 A1 describes an arrangement for the interference suppression of pathogenic areas of irritation with layers of graphite as well as quartz crystal.

CH 687 478 A5 describes an element for screening Earth radiation and rising moisture in a brick wall providing a receptacle that consists of an easily electrically conducting material, wherein said receptacle is filled with granular material. Here e.g. quartz sand can be used.

SUMMARY OF THE INVENTION

The present invention is based on the problem of making a mixture of crystals available that facilitates an increased stimulation of the thymus gland.

According to the invention the problem is solved with the use of a mixture of crystals containing natural ring silicate and natural silicon dioxide for the stimulation of the thymus gland. Here especially rock crystal is used as natural silicon dioxide and/or tourmaline, especially green tourmaline is used as a natural ring silicate.

Preferably the crystals should be arranged in rows, particularly on top of each other. Thereby, the crystals can unfold their piezo-electronic characteristics whereby the green tourmaline polarizes these characteristics. Thereby the required oscillation for stimulation of the thymus gland can be produced.

A special effect can be achieved when the natural silicon dioxide, preferably in the form of rock crystal, and the natural ring silicate, preferably in form of green tourmaline, are used at ratios of 7:1 to 2:1, especially 6:1 to 3:1

Surprisingly, corresponding crystal mixtures show an increased effect on the thymus gland and its stimulation. Demonstrably, kinesiologic measurements showed an effect of a corresponding mixture of crystals on the human body. Furthermore, it could be determined that the effect of electromagnetic radiation on the human body can be reduced through the appropriate mixture of natural ring silicate and natural silicon dioxide, particularly rock crystal and green tourmaline, especially if the mixture is located in direct proximity of a thymus gland. Therefore, the invention also makes reference to the device for shielding or reducing electromagnetic radiation.

Here the silicon dioxide, in particular in the form of rock crystal, and the natural ring silicate, especially in the form of green tourmaline, as the crystal mixture can be arranged in a receptacle equipped with perforations that in turn is designed as a piece of jewelry, and that can be arranged, for example, hanging from a chain in the area of the thymus gland. The mixing ratio of rock crystal and green tourmaline should be, as mentioned above, range from 7:1 to 3:1, in particular 4:1.

The rock crystal and the green tourmaline should have a natural-, chip-, ball-, needle- or button form.

The appropriate crystals should have a maximum length L of 2 mm$\leq$L$\leq$3 mm. The receptacle itself should consist of a precious metal or contain it, preferably silver.

A preferred geometry for the receptacle is that of a cuboid, whereby perforations are provided in at least two longitudinal sides, especially in each longitudinal side, that should have a circular, rectangular or square geometry.

Typical dimensions of a cuboid are: length 20-40 mm, especially approximately 30 mm with a base of 3-7 mm×3-7 mm, especially 5×5 mm$^2$ (sic).

Each sidewall should have at least three to six perforations, whereby a chain can extend through the perforations along the basis and the top.

In order to fill the appropriate cuboid body a receptacle that is enclosed around the circumference and on the bottom and that can be closed by means of a cover element after filling it with crystals is used, whereby said cover element can be glued to the body of the receptacle.

As mentioned above, the receptacle can consist of a precious metal like 925/oo (sic) silver with a rhodium plating, if so desired. Other appropriate materials that do not distort the effect of the crystals are also conceivable.

Precious metals, such as silver, gold or platinum as well as their alloys should be considered.

An appropriate piece of jewelry can be placed—as mentioned above—in the area of the thymus gland, that is, close to the breast-bone. Kinesiologic arm tests according to Dr. Diamond showed that electromagnetic radiation can be greatly shielded or reduced through appropriate devices so that electro-smog exposure can be significantly reduced for a person wearing the appropriate device.

In particular, a stimulation of the thymus gland can occur if the piece of jewelry is close to the area of the thymus gland.

Deviating from the above known suggestions, the materials causing the shielding effect or the stimulation, which are on the one hand natural silicon dioxide, especially rock crystal, and on the other hand natural ring silicate, such as green tourmaline, can be arranged quasi as a pile or also in one another or above each other, whereby the ring silicate should be surrounded by the silicone dioxide. Preferably, however, the crystals are arranged in rows so that the piezo-electric characteristics are completely effective.

In a disk-shaped silicon dioxide the ring silicate should be aligned in the middle, optimizing the desired shielding effect, especially if the volume ratio of silicon dioxide to ring silicate ranges from 3:1 to 7:1.

According to a further development of the invention, the ring silicate is inlaid in the silicon dioxide. As an alternative the ring silicate on be located on the silicon dioxide that has been cut preferably into a disk form.

Apart from that, the volume ratio of the silicon dioxide to the ring silicate should be from 7:1 to 2:1, preferably 6:1 to 3:1.

The amount ratio of the silicon dioxide to the ring silicate should be 7:1 to 2:1, preferably 6:1 to 3:1.

If the ring silicate is arranged above the silicon dioxide, the ring silicate should be centered in relation to the silicon dioxide, whereby a cylindrical form is preferred for the ring silicate whose two faces are preferably at least in part covered by a coating consisting of silver or containing it. Thus, the shielding effect is optimized.

The device in particular should be a piece of jewelry like a pendant whereby the piece of jewelry can have a setting that consists at least in part of a precious metal or contains it. Preferably, the piece of jewelry can be set in silver or a silver alloy. Other precious metals, however, such as gold or platinum or alloys of precious metals should also be particularly emphasized.

BRIEF DESCRIPTION OF THE DRAWINGS

Additional details, advantages and characteristics result not only from the claims and the characteristics gathered from them—either alone and/or in combination—but also from the following description of the design examples shown in the drawing.

They show.

DESCRIPTION OF THE PREFERRED EMBODIMENTS

In FIGS. 1-4, where in principle identical elements are shown with the same reference numbers, different embodiments of devices for the stimulation of the thymus gland or for reducing electromagnetic radiation are shown purely in principle in the form of pieces of jewelry. The representations show pendants, without limiting the invention hereby. Several design options of the device are also possible.

The device according to the invention can also have a plate form in order to be used in the casings or housing walls of cell phones or of electrical equipment in order to achieve the desired shielding effect. As mentioned before, the design of a piece of jewelry should be preferred.

Figure 1:
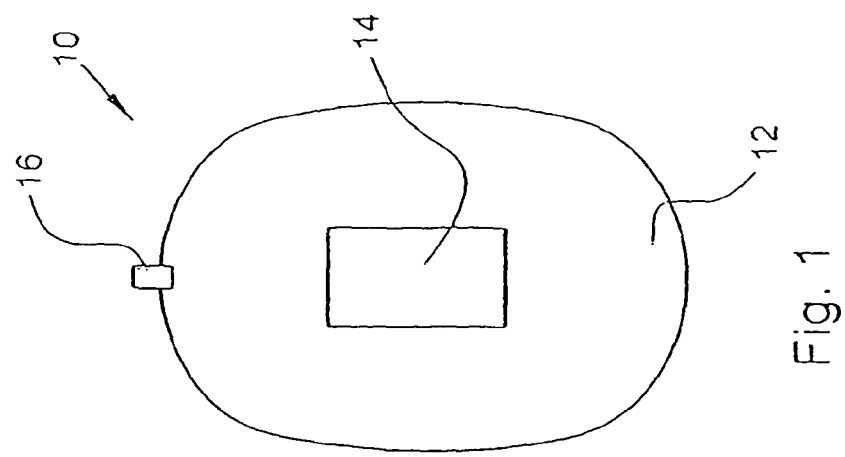
FIG. 1 a view from the above of a device for the stimulation of the thymus gland and/or for shielding or reducing electromagnetic radiation.

A pendant 10 is shown in FIG. 1 consisting of a basic body 12 with a second body 14 located either inside or attached to it that is connected with the basic body 12. The basic body 12 is a natural silicon dioxide, preferably in the form of a rock crystal, whereby the second basic body 12 is a ring silicate such as a green tourmaline.

Hereby the second body 14 is centered in relation to the basic body 12, as can be seen in the basic presentation according to FIG. 1. The volume ratio of the basic body 12 to the second body 14 should range from 7:1 to 3:1, preferably 4:1.

A loop extends from the upper border of the basic body 12 for a chain so that the piece of jewelry 10 can be worn by a person and it can be positioned with such a length that the basic body 12 is located in the area of the thymus gland, meaning the breast bone.

Figure 4:
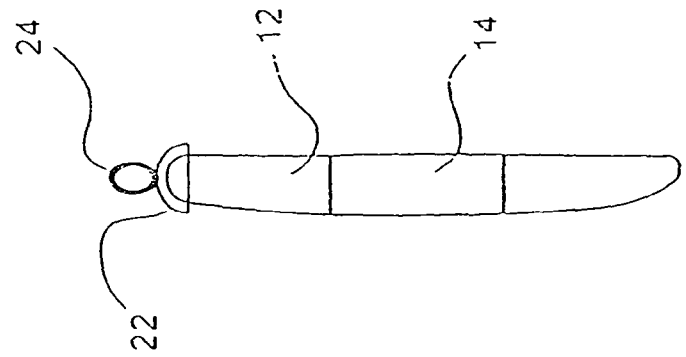
FIG. 4 a third embodiment of a device for the stimulation of the thymus gland and/or for shielding or reducing electromagnetic radiation in a side view.
Figure 3:
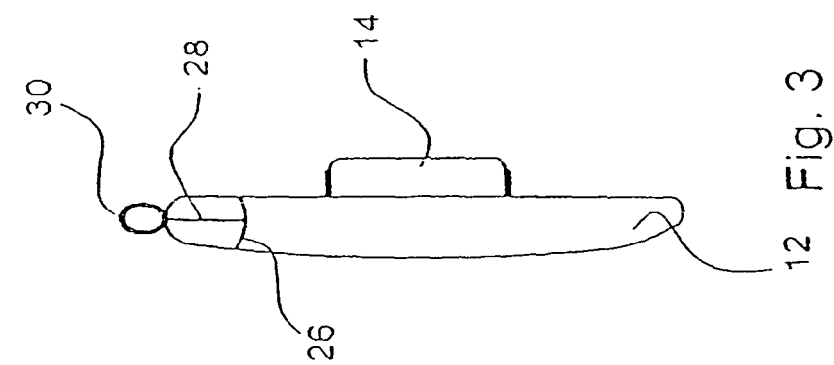
Figure 2:
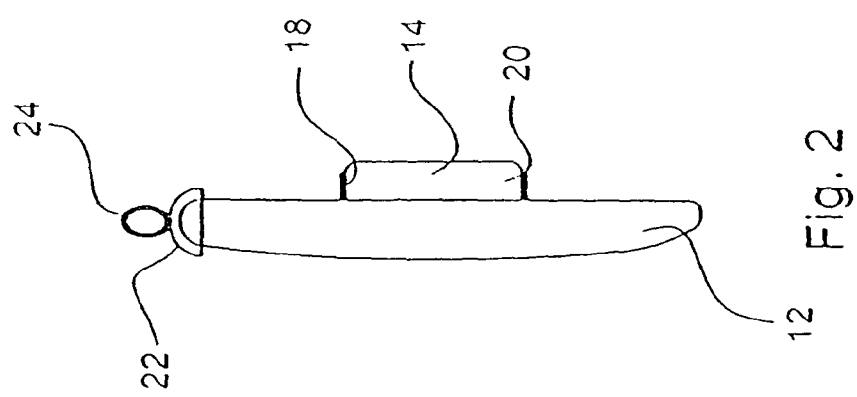
FIG. 2 the device for the stimulation of the thymus gland and/or for shielding or reducing electromagnetic radiation according to FIG. 1 in a side view FIG. 3 a second embodiment of a device for the stimulation of the thymus gland and/or for shielding or reducing electromagnetic radiation in a side view.

As shown in the presentations of FIG. 2 to 4, the second body consisting of a natural ring silicate can be arranged on the basic body (FIGS. 2 and 3) or quasi in it as an inlay.

The second body 14 consisting of natural ring silicate should have a cylindrical form for attachment to the basic body 12, whereby a connection can occur between the second body 14 and the basic body 12 through the use of an adhesive, for example. Other fastening options are also possible. The second body 14 in particular should be covered at its front faces 18, 20 with a precious metal or with an alloy containing a precious metal, thus increasing the shielding effect.

According to the embodiments of FIGS. 2 and 4 the basic body 12 contains at its upper border a clip 22, from which in turn another loop 24 extends corresponding to the loop 16 according to FIG. 1.

In the embodiment of FIG. 3 the basic body 12 consisting of natural silicon dioxide is encapsulated by a ring element 26 adjusted to the cross section of the basic body, from where a bar 28 extends along the circumferential edge of the basic body, which in turn merges into the loop 30 or is connected with it, so that a chain can be threaded through it.

Figure 6:
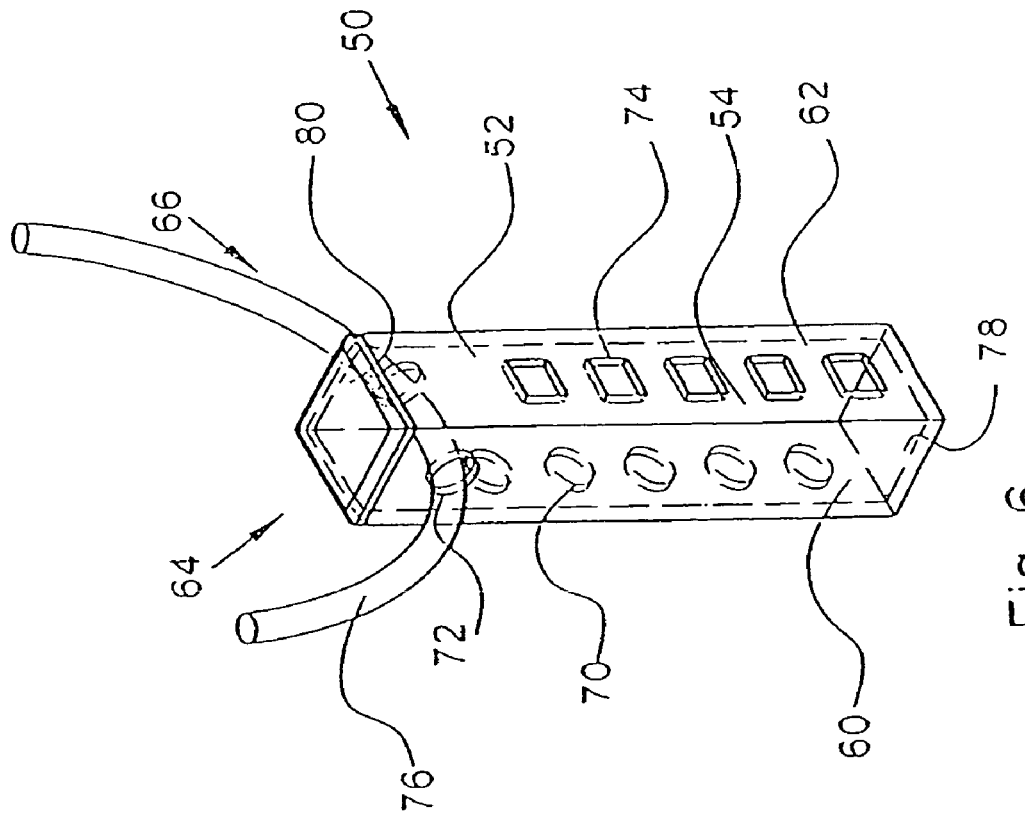
FIG. 6 a housing for the device according to FIG. 5.
Figure 5:
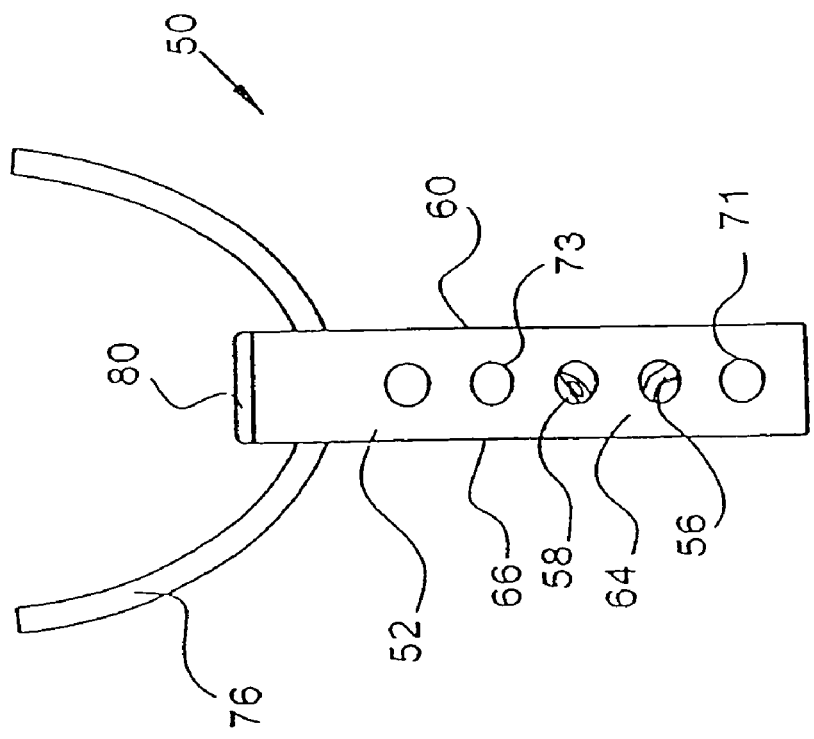
FIG. 5 a preferred embodiment of a device for the stimulation of the thymus gland and/or for shielding or reducing electromagnetic radiation.

FIGS. 5 and 6 depict preferred innovative designs of the tenet according to the invention for the stimulation of the thymus gland and/or for shielding or reducing electromagnetic radiation.

The appropriate device 50 has a receptacle in the form of a cuboid 52 whose internal space 54 is filled with rock crystal 56 and green tourmaline 58, whereby the ratio between the rock crystal 56 and the green tourmaline 58 should range from 7:1 to 3:1, preferably 4:1. The crystals 56, 58 are arranged in the internal space 54 of the housing 52 in such a way that the green tourmaline 58 runs between layers of the rock crystal 56, meaning that the green tourmaline is bordered at the bottom as well as on the top by the rock crystal 56.

Even if the crystals 56, 58 are filled as a pile into the receptacle, it is preferred that the crystals 56, 58 are arranged in rows above each other in order to allow for the complete effect of the piezo-electric characteristics, whereby the green tourmaline polarizes these characteristics. Thus the vibrations necessary for the stimulation of the thymus gland can be produced.

The green tourmaline 58 as well as the rock crystal 56 consist of individual crystals, especially in a natural-, chip-, ball-, needle-, or button form, whereby the maximum length L should amount to about 3 mm$\leq$L$\leq$6 mm.

Perforations 70, 72, 74 are provided in the sidewalls 60, 9J 62, 64, 66. Preferably, circular perforations are provided on three sides—in the embodiment on the sides 60, 64 and 66—and rectangular or square perforations on the remaining side 62.

Furthermore, the top-side perforations 72 in opposite walls 60, 66—in the embodiment in the walls 60, 66—serve as loops for the chain 76. The height of the cuboid receptacle 50 can amount, for example, to 30 mm with a square base or top surface 78, 80 and the border lengths could be 6.5 mm each. These dimensions should not limit the tenet according to the invention.

In reference to the circular perforations 70, 71, 72, 73 a diameter of approximately 2.5 mm can be selected. The border lengths of the rectangular or square perforations 74 could be 2.5 mm. Thus, the walls 60, 62, 64, 66 have sufficient permeability in order to allow an optimal shielding or radiation reduction effect of the rock crystals 56 and the green tourmaline crystals 58.

As can be seen, especially in FIG. 5, the housing 52 can be closed via the wall 80, having practically the function of a cover. If the top wall 80 is removed, the result is a housing open on one side consisting of the side walls 60, 62, 64, 66 and the base wall 78, where the crystals 56, 58 can be filled. After the chain is threaded through the openings 62 at the top wall, the housing 50 can be closed with the top wall 80.

The housing 50 consists, for example, of precious metal, such as 925/oo silver whereby an additional rhodium coating could be provided.

Other precious metals such as gold and platinum or alloys of precious metals can also be considered.

Using FIG. 7a to 7e the characteristics of the crystals arranged in rows should be clarified again. This way it is guaranteed that the crystals remain in contact with each other even in case of agitation so that the piezo-electric characteristics can unfold, whereby the green tourmaline polarizes these characteristics producing the desired vibrations for the stimulation of the thymus gland.

Figure 7:
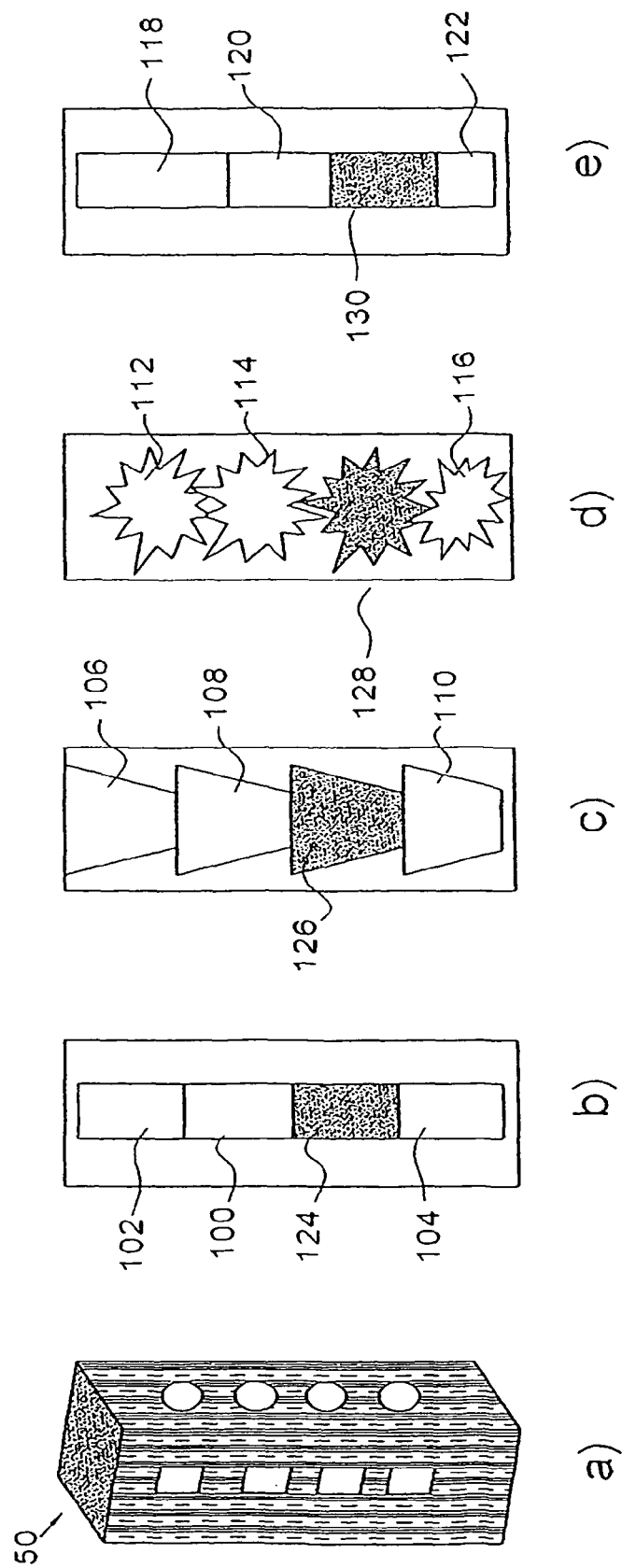
FIGS. 7a-e a housing according to FIG. 6 with basic presentations of crystals arranged in rows.

In FIG. 7 a housing representing a piece of jewelry such as a pendant is shown for accommodating crystals, corresponding to FIGS. 5 and 6. In FIG. 7b to 7c the cross sections of the housing 50 are shown purely in principle with the crystals arranged in rows. The blank bodies 100, 102, 104, 106, 108, 110, 112, 114, 116, 118, 120, 122 represent the rock crystals and the filled bodies 124, 128 and 130 represent the green tourmaline.

It can be seen from the basic presentations that the tourmaline 124, 126, 128, 130 is arranged between two rock crystals 100, 104 or 108, 110 or 120, 12w. There is also contact among the crystals.

The crystals 100, 124 in FIG. 7 can have a square or cylindrical form. The geometry of crystals 106, 108, 110, 126 in FIG. 7 is tapered, whereby the smaller base surface is supported by a larger base surface.

The symbols of the crystals 112, 114, 126, 128 according to FIG. 7e symbolize the accumulations of crystals that consequently can form a pile each. Independent from it, the function according to the invention is guaranteed by the pile, which is likewise arranged in crystal rows. The crystals can also be used in the form of balls.

Finally, FIG. 7e symbolizes that the crystals 118, 120, 122, 130 can have lengths that differ from each other.

The invention claimed is:

1. A device comprising a receptacle in cuboid form having openings in at least two longitudinal walls thereof, and having therein crystals of natural silicon dioxide in form of rock crystal and crystals of natural ring silicate in form of tourmaline, the crystals being arranged in piles or rows of rock crystal and piles or rows of tourmaline, the piles or rows disposed beside or on top of each other, the rock crystal and tourmaline being present in a weight ratio of 7:1 to 3:1.

2. Device according to claim 1, wherein the tourmaline is green tourmaline.

3. Device according to claim 1, wherein the rock crystal and the tourmaline are present in a weight ratio of 6:1 to 4:1.

4. Device according to claim 1, wherein the crystals are in at least one form selected from the group consisting of natural form, chip form, ball form, needle form, and button form, and are arranged in layers.

5. Device according to claim 1, wherein a plurality of crystals of the rock crystal and at least one crystal of tourmaline are arranged in the receptacle, at least one of 1) the crystals of rock crystal and 2) the crystal of tourmaline having a maximum length L of $2 \text{ mm} \leq L \leq 3 \text{ mm}$.

6. Device according to claim 1, wherein the receptacle comprises precious metal selected from the group consisting of gold, silver, platinum and alloys thereof.

7. Device according to claim 6, wherein the precious metal is silver, optionally coated with rhodium.

8. Device according to claim 1, wherein each longitudinal wall of the receptacle has openings.

9. Device according to claim 1, wherein the cuboid has at least one of 1) a closed base wall and 2) a closed top wall.

10. Device according to claim 1, wherein the openings have a geometry of at least one of 1) circles and 2) quadrangles.

11. Device according to claim 1, wherein the receptacle is a pendant including a chain.

* * * * *